United States Patent
Soltz et al.

(10) Patent No.: US 8,734,730 B2
(45) Date of Patent: May 27, 2014

(54) SURGICAL INSTRUMENT DEBRIS COLLECTION SYSTEM

(75) Inventors: Michael A. Soltz, Hamden, CT (US);
Joshua Stopek, Yalesville, CT (US);
Wojciech Kisiel, North Haven, CT (US);
Jennifer Broom, Branford, CT (US)

(73) Assignee: Covidien LP, Mansfield, MA (US)

( * ) Notice: Subject to any disclaimer, the term of this patent is extended or adjusted under 35 U.S.C. 154(b) by 1068 days.

(21) Appl. No.: 11/731,409

(22) Filed: Mar. 30, 2007

(65) Prior Publication Data

US 2008/0237074 A1    Oct. 2, 2008

(51) Int. Cl.
*A61L 2/00* (2006.01)
*A61L 9/00* (2006.01)
*B65D 83/10* (2006.01)
*A61B 17/06* (2006.01)
*A61B 19/02* (2006.01)
*A61L 15/00* (2006.01)

(52) U.S. Cl.
USPC ........... 422/300; 422/292; 422/301; 206/363; 206/438

(58) Field of Classification Search
USPC ............... 206/368, 369, 63.5, 269, 363, 438; 422/292, 300, 301
See application file for complete search history.

(56) References Cited

U.S. PATENT DOCUMENTS

| | | | |
|---|---|---|---|
| 3,209,388 A * | 10/1965 | Kambersky | 401/128 |
| 3,782,610 A | 1/1974 | Gilbert | |
| 3,844,275 A | 10/1974 | Elliott | |
| 4,335,756 A | 6/1982 | Sharp et al. | |
| 4,446,967 A | 5/1984 | Halkyard | |
| 4,702,396 A * | 10/1987 | Gwiazda | 222/152 |
| 5,102,010 A * | 4/1992 | Osgar et al. | 222/1 |
| 5,308,406 A | 5/1994 | Wallock | |
| 5,458,165 A * | 10/1995 | Liebmann, Jr. | 141/64 |
| 5,471,706 A | 12/1995 | Wallock et al. | |
| 5,518,115 A * | 5/1996 | Latulippe | 206/370 |
| 5,752,286 A | 5/1998 | Wright | |
| 5,853,096 A * | 12/1998 | Bartur et al. | 215/261 |
| 5,879,288 A * | 3/1999 | Suzuki et al. | 600/176 |
| 5,894,015 A | 4/1999 | Rechtin | |

(Continued)

FOREIGN PATENT DOCUMENTS

DE    4 323 816 A1    1/1995
DE    43 23 816 A1    1/1995

(Continued)

OTHER PUBLICATIONS

European Search Report for EP 08221194.0-2310 date of completion is Jun. 20, 2008 (10 pages).

*Primary Examiner* — Regina M Yoo

(57) ABSTRACT

The presently disclosed debris collection system includes an elongate body having a first end, a second end, and a bore extending therethrough. The first end of the elongate body is hermetically closed while the second end has an opening. The elongated body is made of an impermeable material. A cap fixed to the elongated body and has a bore extending therethrough. A port, which is attached to the cap, is designed for introducing fluid into the elongated body. A watertight seal, such as a gasket, is attached to the cap. The seal is also made of an impermeable material. In operation, a liquid is introduced into the debris collection system. A surgical tool must then be introduced into the system. Thereafter, a vortex is created within the system to debride debris from the surgical tool.

16 Claims, 3 Drawing Sheets

(56) References Cited

U.S. PATENT DOCUMENTS

| | | |
|---|---|---|
| 5,902,547 A | 5/1999 | Hill |
| 5,961,937 A | 10/1999 | Gobbato |
| 5,989,183 A | 11/1999 | Reisdorf et al. |
| 6,110,103 A | 8/2000 | Donofrio |
| 6,186,325 B1 | 2/2001 | Schmidt et al. |
| 6,187,265 B1 | 2/2001 | Wu et al. |
| 6,305,591 B1 * | 10/2001 | Jones ............................ 224/601 |
| 6,357,589 B2 | 3/2002 | Schmidt et al. |
| 6,367,110 B1 | 4/2002 | Urueta et al. |
| 6,551,238 B2 | 4/2003 | Staud |
| 6,793,882 B1 | 9/2004 | Verschuur |
| 7,121,098 B2 * | 10/2006 | Hatcher .............................. 62/5 |
| 2002/0049426 A1 * | 4/2002 | Butler et al. ................ 604/892.1 |
| 2002/0145000 A1 * | 10/2002 | Li ................................ 220/709 |
| 2003/0026729 A1 | 2/2003 | Wu et al. |
| 2004/0216468 A1 * | 11/2004 | Hatcher .............................. 62/5 |
| 2004/0258559 A1 | 12/2004 | Paskal et al. |
| 2005/0143625 A1 | 6/2005 | Whitmore, III et al. |
| 2005/0147773 A1 * | 7/2005 | Saliaris et al. ................ 428/34.1 |
| 2005/0218022 A1 | 10/2005 | Cervantes |
| 2005/0236459 A1 | 10/2005 | Gresham |
| 2006/0020165 A1 | 1/2006 | Adams |
| 2006/0052662 A1 | 3/2006 | Kress |
| 2006/0135962 A1 * | 6/2006 | Kick et al. ..................... 606/108 |
| 2006/0217693 A1 * | 9/2006 | Gowda et al. .................... 606/15 |
| 2007/0102044 A1 * | 5/2007 | Patzek .......................... 137/212 |
| 2008/0242927 A1 * | 10/2008 | Hirata .......................... 600/109 |

FOREIGN PATENT DOCUMENTS

| | | |
|---|---|---|
| EP | 1 398 004 A | 3/2004 |
| EP | 1 398 004 A | 3/2004 |
| WO | WO 03/041747 A | 5/2003 |
| WO | WO 03/041747 A | 5/2003 |

* cited by examiner

SURGICAL INSTRUMENT DEBRIS COLLECTION SYSTEM

BACKGROUND

1. Technical Field

The present disclosure relates to a collection system for surgical instruments. More particularly, the present disclosure relates to a staple cartridge debris collection system.

2. Background of Related Art

During routine surgical procedures, medical instruments can accumulate organic and inorganic debris. This debris may contain healthy tissue, diseased tissue, or tissue debris which contains pathogens or other dangerous substances. Surgeons, nurses, and other health care professionals must therefore take the necessary measures to avoid contamination. Even if a medical instrument, or a portion thereof, is disposable, these professionals have to debride the debris from the medical instrument before handling it to prevent infections. Direct and, sometimes indirect, contact with tissue debris may cause illnesses. Health care professionals must thus dislodge debris from a medical instrument before disposing or reusing it.

In an effort to prevent contamination, many devices, systems and methods have been developed over the years to debride debris from surgical and dental instruments. Hand-scrubbing, for instance, is one of the methods used for debridement. This method involves the use of friction to dislodge and remove solids accumulated in a surgical instrument. To apply friction to medical or dental equipment, technicians typically employ a hand-held bristle brush such as a bristle nail brush or a tooth brush. In theory, the constant and frequent hand scrubbing with the hand-held brush removes organic and inorganic debris from the surgical instrument. Hand-scrubbing, however, does not necessarily control or prevent infections because it may lead to direct contact with contaminated surfaces.

More recently, ultrasonic cleaning has been used to debride debris from medical instruments. This method reduces the likelihood of direct staff contact with contaminated surfaces. In this method, instruments are placed in a chamber and submerged in a suitable ultrasound conducting fluid. An ultrasonic generating transducer is then electronically activated to produce ultrasonic waves in the fluid. Consequently, energy is released from the creation and collapse of microscopic cavitation bubbles. These bubbles break up and lift off dirt and contaminants from the instrument's surface. Ultrasonic cleaning, however, requires machinery, expensive maintenance, and considerable expenditure of time in its practice.

The debris removal methods described hereinabove have their disadvantages. Hand-scrubbing does not effectively prevent infections, and ultrasonic cleaning can be very expensive. In light of the foregoing, it is desirable to develop an efficient and inexpensive device, system, and method for debriding debris from medical instruments.

SUMMARY

In accordance with the present disclosure, a debris collection system is provided that includes an elongated body having a first end, a second end, and a bore extending therethrough. The first end of the elongated body is hermetically closed while the second end has an opening. The elongated body, which is fixed to a cap, is made of an impermeable material.

The cap has a bore extending therethrough. The bore of the cap is dimensioned to receive a surgical tool. A port for introducing fluid into the elongated body is attached to the cap. This port can be relatively movable between an open and a closed position. In addition to the port, a seal is attached to the cap. The seal can be a gasket or any other suitable watertight seal known in the art and it is composed of an impermeable material. The system may include a port for removing a sample of fluid from the elongated body.

During operation, a liquid is introduced into the debris collection system. Then, a surgical tool is inserted in the system. To remove debris from the tool, a vortex is created within the elongated body of the debris collection system. The vortex may be created in a number of ways. For example, gas may be delivered to the debris collection system from an external source. The delivery of gas will produce a turbid flow within the elongated body and thereby debride debris from the surgical tool.

BRIEF DESCRIPTION OF THE DRAWINGS

Embodiments of the presently disclosed staple cartridge debris collection system are described herein with reference to the accompanying drawings, wherein.

DETAILED DESCRIPTION OF THE DRAWINGS

Figure 2:
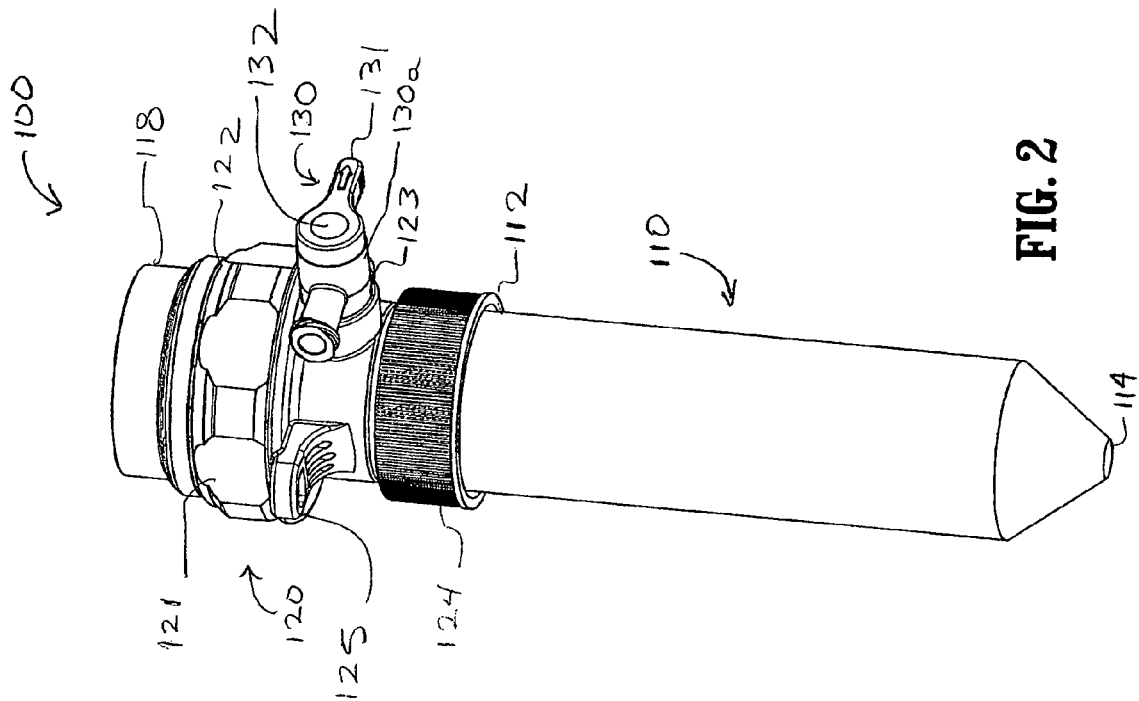
FIG. 2 is a perspective view of the staple cartridge debris collection system of FIG. 1.

Embodiments of the present disclosure will now be described in detail with reference to the drawings wherein like reference numerals identify similar or identical elements. In the drawings and in the description that follows, the term "proximal," as is traditional, will refer to the end of the staple cartridge debris collection system that is closest to the operator while the term "distal" will refer to the end of the collection system that is farthest from the operator.

Figure 1:
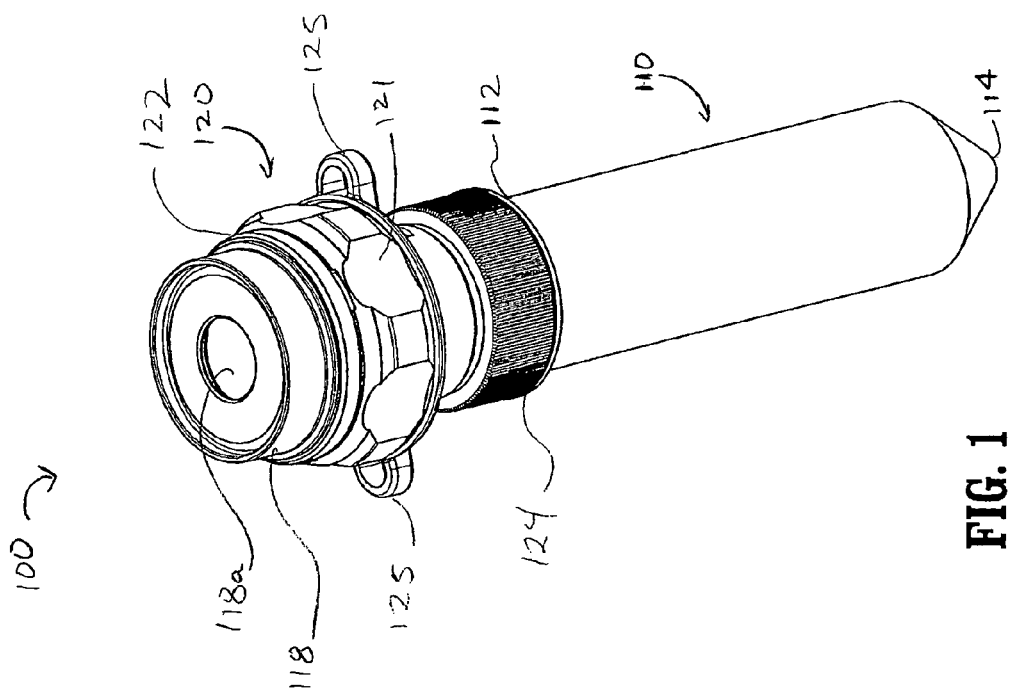
FIG. 1 is a perspective view of a staple cartridge debris collection system constructed according to an embodiment of the present disclosure.

The present disclosure relates to a debris collection system to remove debris from a tool of a surgical stapling apparatus or any other suitable medical instrument. Referring to FIGS. 1-2, a debris collection system, in accordance with an embodiment of the present disclosure, is generally designated as 100.

As seen in FIGS. 1-2, debris collection system 100 includes an elongated body 110 and a cap 120 attached thereto. Elongated body 110 has a proximal end 112, a distal end 114, and a bore 116 extending therethrough. (See FIG. 5). Bore 116 is adapted and dimensioned to receive a surgical tool of a surgical stapling instrument. Despite the latter, a person with ordinary skill in the art will understand that bore 116 may be configured to receive any suitable medical device. The distal end 114 of elongated body 110 is hermetically closed while the proximal end 112 of the elongated body 110 has an opening 113. (See FIG. 4.) Elongated body 110 is made of an impermeable material and, consequently, fluids can only enter or exit elongated body 110 through opening 113. Although the figures illustrate a distal end 114 with a substantially conical shape, it is envisioned that distal end 114 may have any suitable shape. The proximal opening 113 of elongated body 110 is substantially aligned with a bore 127 extending through a cap 120. (See FIG. 4.)

Cap 120 is releasably secured to the proximal end 112 of the elongated body 110 and includes a proximal end 122, a distal end 124, and a bore 127 for receiving an access port 130. The distal end 124 of cap 120 is fixed to the proximal end 112 of elongated body 110. Additionally, cap 120 has indentations 121 around its perimeter for receiving the user's fingers. An embodiment of debris collection system 100 includes at least one hook 125 positioned on the external surface of cap 120 to facilitate handling thereof.

In one embodiment, a user can secure cap 120 to elongated body 112 by positioning its fingers on indentations 121 and rotating cap 120. This embodiment includes a proximal end 112 of elongated body 100 having a threaded external wall and a distal end 124 of cap 120 having a threaded inner wall as well. These threaded walls engage with each other during operation to secure or release cap 120 from elongated body 110. Particularly, a user may secure cap 120 to elongated body 110 by rotating cap 120 clockwise. In turn, the user may also loosen or separate cap 120 from elongated body 110 by turning cap 120 counterclockwise. In other embodiments, the cap is removably connected to the elongated body by a bayonet, snap-fit, or other means.

Figure 3:
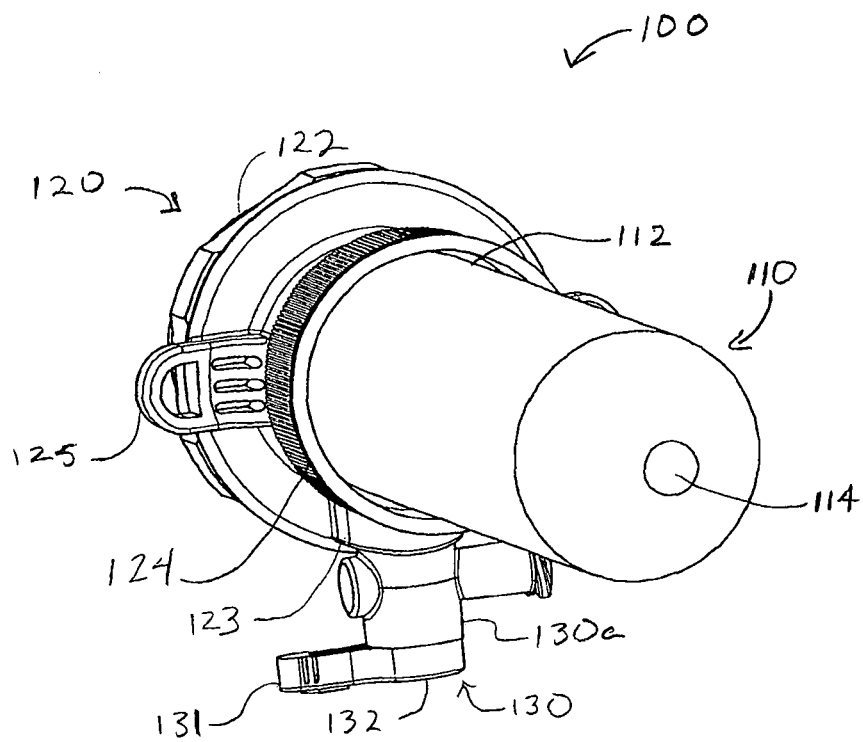
FIG. 3 is a perspective view of the staple cartridge debris collection system of FIGS. 1-2.
Figure 4:
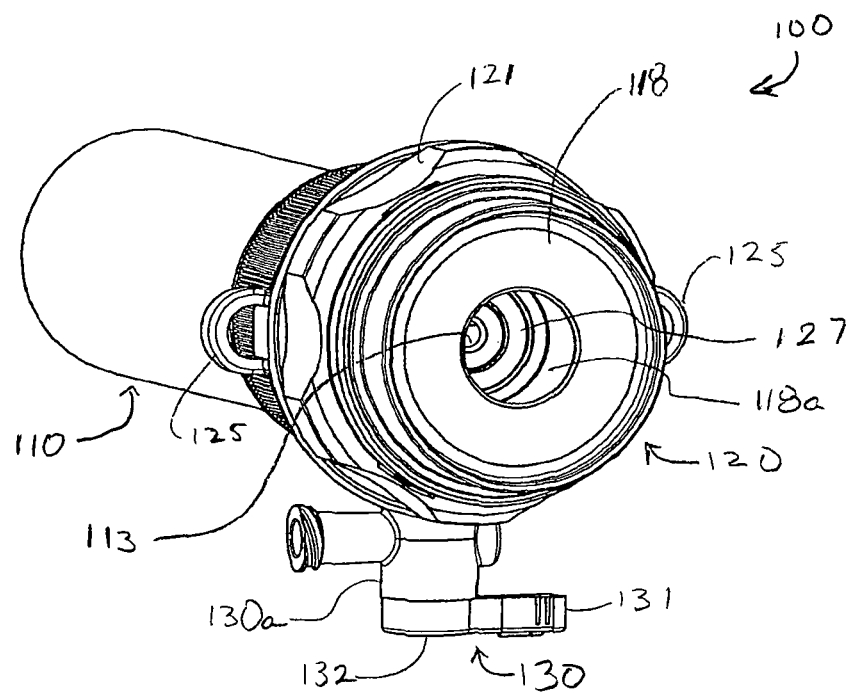
FIG. 4 is a perspective view of the staple cartridge debris collection system of FIGS. 1-3.

With reference to FIGS. 3-4, cap 120 includes an aperture 123 adapted to receive an access port 130. Access port 130 provides fluid communication between an external source 140 (see FIG. 5) and elongated body 110 through at least one opening 132. Additionally, access port 130 is relatively movable between an open position and a closed position. When access port 130 is in its open position, fluids can freely travel between external source 140 and elongated body 110. Conversely, external source 140 and elongated body 110 are not in fluid communication with each other when access port 130 is in its closed position.

In an embodiment, a user can turn access port 130 to switch between the open position and the closed position. The access port 130 of this embodiment includes a projection 131 to facilitate rotation of the access port 130. Projection 131 extends outwardly from a body 130a of access port 130.

A watertight seal 118 is positioned on the proximal end 122 of cap 120. Seal 118 includes an opening 118a for receiving a surgical tool of a surgical stapling instrument or any other suitable medical instrument. Further, seal 118 may be a gasket or any other suitable watertight seal known in the art. An impermeable material may be used to construct seal 118 to prevent liquids from escaping the debris collection system 100.

Figure 5:
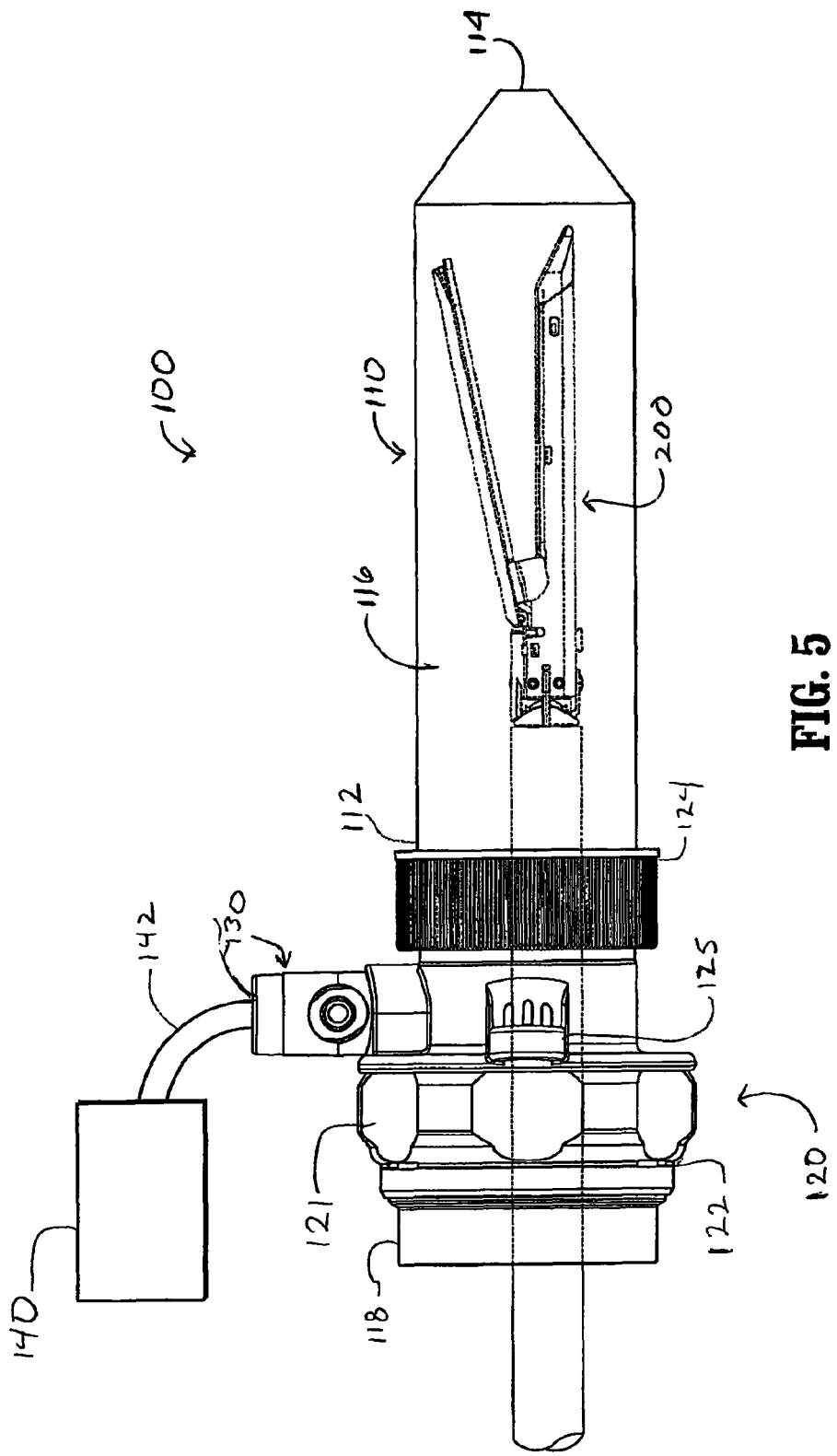
FIG. 5 is a side elevational view of the staple cartridge debris collection system of FIGS. 1-4 including a surgical tool disposed therein and a fluid source attached thereto.

In operation, a user injects, or pours, the desired tissue media, sterilizing fluid, antimicrobial agent or any other suitable fluid known in the art into elongated body 110 through access port 130. A tube 142 or other conducting medium may be used to transport the desired fluid from an external source 140 to access port 130. A stapler head, a stapler cartridge, or a surgical tool 200 is then inserted into debris collection system 100 via bore 127 of cap 120, as illustrated in FIG. 5. Thereafter, the user must create a vortex inside elongated body 110 to effectively debride debris from the inserted tool 200. The vortex can be created by inserting air or any other suitable gas into elongated body 110. Additionally or alternatively, the system can be mechanically agitated. An apparatus, such as external source 140, may be used to provide gas to elongated body 110 and create a vortex therein. The delivery of gas into the elongated body 110 will produce turbid flow within the elongated body 110. Once the debris had been debrided from the surgical tool 200, the user may remove surgical tool 200 from debris collection system 100 and place a standard cap over surgical tool 200.

It will be understood that various modifications can be made to the embodiments of the presently disclosed debris collection system. Therefore, the above description should not be construed as limiting, but merely as exemplifications of embodiments. Those skilled in the art will envision other modifications within the scope and spirit of the present disclosure.

What is claimed is:

1. A debris collection system, comprising:
    an elongated body having a first end and a second end, the elongated body including a channel extending partially therethrough for receiving a surgical tool, wherein the second end of the elongated body has an opening;
    a cap releasably secured to the elongated body, the cap having a bore extending therethrough, the bore being configured to receive the surgical tool therethrough;
    an external source of gas; and
    a port attached to the cap, the port being rotatable between open and closed positions independent of relative axial positions of the elongated body and the cap, the port being rotatable between open and closed positions regardless of the presence of the surgical tool in the channel of the elongated body and the bore of the cap, the port being in fluid communication with the elongated body when in the open position during which the gas is supplied through the port;
    wherein the cap and the elongated body are configured to retain a fluid contained within the channel of the elongated body when the gas is supplied into the channel, and supplying the gas to the fluid in the elongated body to cause a turbid flow within the elongated body.

2. The debris collection system according to claim 1, wherein the port is configured for removing a fluid sample from the elongated body.

3. The debris collection system according to claim 1, further comprising a fluid removal port.

4. The debris collection system according to claim 1, further comprising a seal attached to the cap.

5. The debris collection system according to claim 4, wherein the seal is a gasket.

6. The debris collection system according to claim 4, wherein the seal is composed of an impermeable material.

7. The debris collection system according to claim 1, wherein the elongated body is made of an impermeable material.

8. A debris collection system, comprising:
    an elongated body having a first end, a second end, and a channel extending therethrough, wherein the first end of the elongated body is hermetically closed and the second end of the elongated body has an opening;
    a cap fixed to the second end of the elongated body, the cap having a bore extending therethrough, the bore being configured to receive a surgical instrument therethrough;
    a first external source of fluid to supply a first fluid;
    a second external source of fluid to supply a second fluid; and
    a port attached to the cap, the port being rotatable between open and closed positions independent of an axial position of the cap with respect to the elongated body, the elongated body and the first external source being in fluid communication when the port is in the open position during which the first fluid is supplied through the port from the first external source of fluid, wherein the channel of the elongated body is configured to receive the surgical instrument through the bore of the cap, and the port is operable regardless of the presence of the surgical instrument in the channel of the elongated body and the bore of the cap;

wherein the debris collection system is configured to retain the first fluid therein when the second fluid is supplied into the channel, and to supply the second fluid into the channel containing the first fluid to cause a vortex in the fluids.

9. The debris collection system according to claim 8, wherein the port is configured for removing a fluid sample from the elongated body.

10. The debris collection system according to claim 8, further comprising a fluid removal port.

11. The debris collection system according to claim 8, further comprising a seal attached to the cap.

12. The debris collection system according to claim 11, wherein the seal is a gasket.

13. The debris collection system according to claim 11, wherein the seal is composed of an impermeable material.

14. The debris collection system of claim 11, wherein the seal is positioned on a proximal end portion of the cap.

15. The debris collection system of claim 11, wherein the seal includes an opening in communication with the bore of the cap for receiving the surgical instrument therethrough.

16. The debris collection system according to claim 8, wherein the elongated body is made of an impermeable material.

* * * * *